(12) United States Patent
Park et al.

(10) Patent No.: US 11,119,075 B2
(45) Date of Patent: Sep. 14, 2021

(54) GAS SENSOR AND GAS SENSING METHOD FOR PROVIDING SELF-CALIBRATION

(71) Applicant: Samsung Electronics Co., Ltd., Suwon-si (KR)

(72) Inventors: Jeong-ho Park, Seoul (KR); Eun-je Hyun, Seoul (KR); Kwang-min Park, Daejeon (KR); Min-chul Lee, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 117 days.

(21) Appl. No.: 16/414,029

(22) Filed: May 16, 2019

(65) Prior Publication Data

US 2020/0110060 A1  Apr. 9, 2020

(30) Foreign Application Priority Data

Oct. 5, 2018  (KR) .......................... 10-2018-0119307

(51) Int. Cl.
*G01N 29/30* (2006.01)
*G01N 29/036* (2006.01)
(Continued)

(52) U.S. Cl.
CPC .......... *G01N 29/30* (2013.01); *G01N 29/022* (2013.01); *G01N 29/036* (2013.01); *G01N 33/0006* (2013.01); *G01N 2291/0426* (2013.01)

(58) Field of Classification Search
CPC .... G01N 29/30; G01N 29/036; G01N 29/022; G01N 2291/0426; G01N 2291/0256
See application file for complete search history.

(56) References Cited

U.S. PATENT DOCUMENTS 3,729,982 A * 5/1973 Senda ................... G01N 29/02
73/32 A
5,329,804 A * 7/1994 Germany ............. A61B 5/1491
73/1.06
(Continued)

FOREIGN PATENT DOCUMENTS

JP  2005308403 A  * 11/2005
JP  3966143 B2  8/2007
(Continued)

OTHER PUBLICATIONS (Humberto Campanella, Thin-film bulk acoustic wave resonators—FBAR: Fabrication, heterogeneous integration with CMOS technologies and sensor applications, Universite de Montpellier II (UM2) and Universitat Autonoma de Barcelona (UAB), 2007 (Year: 2007).*

*Primary Examiner* — Peter J Macchiarolo
*Assistant Examiner* — Fatemeh Esfandiari Nia
(74) *Attorney, Agent, or Firm* — Harness, Dickey & Pierce, P.L.C.

(57) ABSTRACT

A gas sensor including a gas sensing device having a resonant frequency that varies with adsorbed chemicals, a frequency detector configured to detect the resonant frequency of the gas sensing device, a calibrator configured to generate current calibration data based on the resonant frequency of the gas sensing device which has been heated to a calibration temperature in a calibration mode, and a compensator configured to adjust an output value of the frequency detector based on the current calibration data in a sensing mode may be provided.

19 Claims, 14 Drawing Sheets

(51) Int. Cl.
*G01N 29/02* (2006.01)
*G01N 33/00* (2006.01)

(56) References Cited

U.S. PATENT DOCUMENTS

| | | | |
|---|---|---|---|
| 6,720,534 B2 | 4/2004 | Hada et al. | |
| 8,390,387 B2* | 3/2013 | Lander | H03H 9/2405 |
| | | | 331/154 |
| 2003/0037590 A1 | 2/2003 | Stark | |
| 2005/0017738 A1* | 1/2005 | Lin | G01N 33/2888 |
| | | | 324/698 |
| 2006/0125489 A1* | 6/2006 | Feucht | G01N 29/022 |
| | | | 324/633 |
| 2008/0298427 A1* | 12/2008 | Gabi | G01N 29/036 |
| | | | 374/119 |
| 2009/0120169 A1* | 5/2009 | Chandler, Jr. | G01N 9/002 |
| | | | 73/54.41 |
| 2017/0138878 A1 | 5/2017 | Jun | |
| 2019/0072523 A1* | 3/2019 | Britt | G01N 29/022 |
| 2019/0265177 A1* | 8/2019 | Kukita | G01N 5/04 |
| 2019/0339232 A1* | 11/2019 | Kolb | G01N 29/2437 |

FOREIGN PATENT DOCUMENTS

| | | |
|---|---|---|
| JP | 4871776 B2 | 2/2012 |
| JP | 5795998 B2 | 10/2015 |
| JP | 2017-181301 A | 10/2017 |
| KR | 10-2002-0020715 | 3/2002 |

* cited by examiner

GAS SENSOR AND GAS SENSING METHOD FOR PROVIDING SELF-CALIBRATION

CROSS-REFERENCE TO RELATED APPLICATION

This application claims the benefit of Korean Patent Application No. 10-2018-0119307, filed on Oct. 5, 2018, in the Korean Intellectual Property Office, the disclosure of which is incorporated herein in its entirety by reference.

BACKGROUND

The inventive concepts relate to gas sensors, and more particularly, to gas sensors and/or gas sensing methods for providing self-calibration.

Gas sensors may be used for various applications. For example, a gas sensor may be mounted on an air purifier, and used to measure air quality around the air purifier. Also, the gas sensor may be included in a portable device such as a mobile phone and used in order for a user of the portable device to recognize the quality of ambient air. The gas sensor may include a gas sensing device that senses gas according to various principles, and the gas sensing device may have an exposed surface for sensing gas. Sensitivity of the gas sensing device may vary due to humidity, heat, and gas accumulation amount applied to the gas sensing device during use of the gas sensor, and accordingly the accuracy of the gas sensor may be reduced.

SUMMARY

The inventive concepts relate to gas sensors for accurately sensing gas and provide gas sensors and/or gas sensing methods for providing self-calibration.

According to an example embodiment, a gas sensor includes a gas sensing device having a resonant frequency that varies with adsorbed chemicals, and processing circuitry. The processing circuitry may be configured to detect the resonant frequency of the gas sensing device, generate current calibration data based on the resonant frequency of the gas sensing device which has been heated to a calibration temperature in a current calibration mode, and adjust an output value thereof based on the current calibration data in a sensing mode.

According to an example embodiment, a gas sensor includes a gas sensing device having a resonant frequency that varies with adsorbed chemicals, a heater configured to heat the gas sensing device, and a controller. The controller may be configured to control the heater such that the gas sensing device reaches a calibration temperature and generate calibration data based on the resonant frequency in a current calibration mode, and detect gas based on the calibration data and the resonant frequency in a sensing mode.

According to an example embodiment, a method of sensing gas includes heating a gas sensing device, which has a resonant frequency that varies with adsorbed chemicals, to a calibration temperature in a current calibration mode, generating current calibration data based on the resonant frequency of the heated gas sensing device, in the current calibration mode, and detecting gas based on the current calibration data and the resonant frequency of the gas sensing device as to which the heating has been stopped, in a sensing mode.

BRIEF DESCRIPTION OF THE DRAWINGS

Some example embodiments of the inventive concepts will be more clearly understood from the following detailed description taken in conjunction with the accompanying drawings in which.

DETAILED DESCRIPTION

Figure 1:
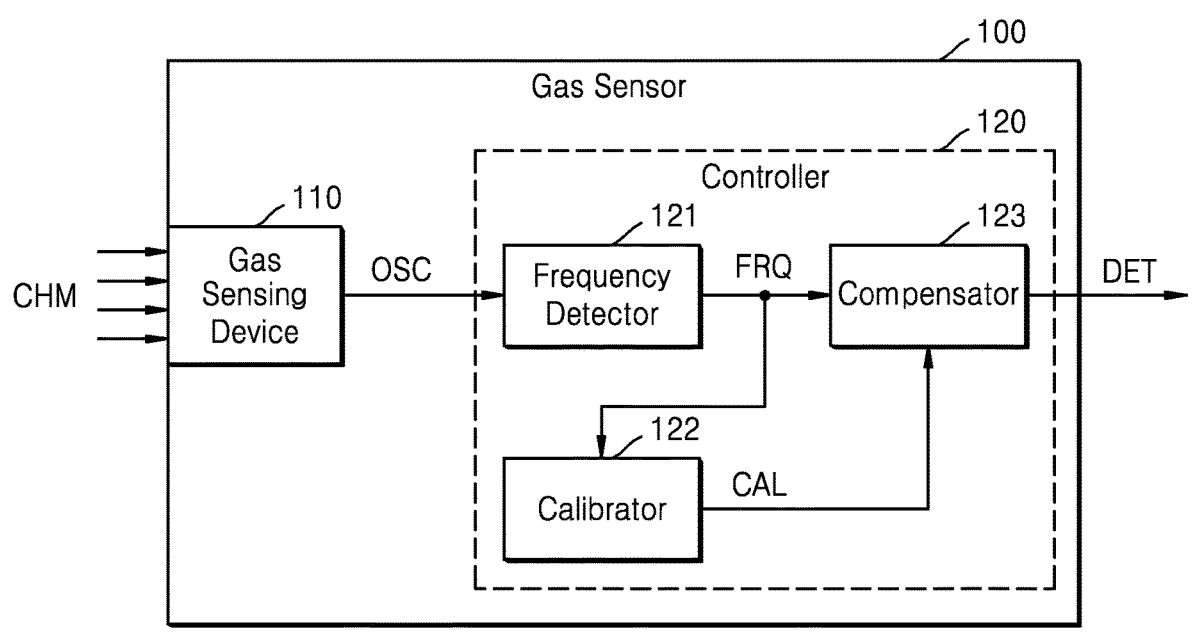
FIG. 1 is a block diagram of a gas sensor according to an example embodiment.

FIG. 1 is a block diagram of a gas sensor 100 according to an example embodiment. The gas sensor 100 may generate a detection signal DET by sensing chemicals CHM in a gas phase, and the detection signal DET may include information about the concentration of the chemicals CHM. As shown in FIG. 1, the gas sensor 100 may include a gas sensing device 110 and a controller 120.

The gas sensing device 110 may have an exposed surface exposed to the outside of the gas sensor 100 and may generate an output signal OSC that depends on the chemicals CHM adsorbed on the exposed surface. The gas sensing device 110 may sense the chemicals CHM according to various principles. In some example embodiments, the gas sensing device 110 may have a resonant frequency that varies with the concentration of the chemicals CHM (e.g., the amount of adsorbed chemicals CHM), and accordingly, the frequency of the output signal OSC may depend on the concentration of the chemicals CHM. For example, as described below with reference to FIGS. 2A and 2B, the gas sensing device 110 may include a film bulk acoustic resonator (FBAR). Examples of the gas sensing device 110 are described below with reference to FIGS. 2A and 2B.

Because the gas sensing device 110 has an exposed surface on which the chemicals CHM are adsorbed, the characteristics of the gas sensing device 110 may change due to various causes. For example, as described below with reference to FIGS. 3A and 3B, the relationship between the concentration of the chemicals CHM and the frequency of the output signal OSC may be changed due to moisture, heat, etc. applied to the gas sensing device 110 during use of the gas sensor 100, and accordingly, the detection signal DET output from the gas sensor 100 may not accurately reflect the concentration of the chemicals CHM. As described below, the gas sensor 100 according to some example embodiments may compensate for a change in the characteristics of the gas sensing device 110 via self-calibration, and accordingly the gas sensor 100 may continuously and accurately detect the chemicals CHM. Further, because the self-calibration may be performed independently of the ambient environment of the gas sensor 100 (e.g., the concentration of the chemicals CHM), the gas sensor 100 may be easily calibrated at a desired point in time. Thus, the gas sensor 100 may have an extended service life.

The controller 120 may receive the output signal OSC from the gas sensing device 110 and may generate the detection signal DET based on the output signal OSC. In some example embodiments, the detection signal DET may include a plurality of bits representing the concentration of the chemicals CHM. As shown in FIG. 1, the controller 120 may include a frequency detector 121, a calibrator 122, and a compensator 123. The frequency detector 121, the calibrator 122, and the compensator 123 may be functional units of the controller 120. However, the controller 120 are not intended to be limited to the disclosed functional units. For example, in some example embodiments, additional functional units may be included in the controller 120. Further, the controller 120 may perform the operations and/or functions of the various functional units without sub-dividing the operations and/or functions of the various functional units into these various functional units.

Each of the components included in the controller 120 and the controller 120 may be processing circuitry such as hardware including logic circuits, a processing unit including software and a core executing the software, or a combination of the hardware and the processing unit. For example, the processing circuitry may include, but is not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

The frequency detector 121 may detect the frequency of the output signal OSC and generate a frequency signal FRQ corresponding to the frequency of the output signal OSC. The frequency detector 121 may have any structure for detecting the frequency of the output signal OSC. For example, the frequency detector 121 may receive a reference clock from an oscillator having a reference frequency and may detect the frequency of the output signal OSC by comparing the reference clock with the output signal OSC. Further, the frequency detector 121 may include a counter and may detect the frequency of the output signal OSC by counting the edges of the output signal OSC for a certain period of time. In some example embodiments, the frequency signal FRQ may include a plurality of bits representing the frequency of the output signal OSC.

The calibrator 122 may receive the frequency signal FRQ from the frequency detector 121, and may generate calibration data CAL and provide it to the compensator 123. The gas sensor 100 may be switched between a sensing mode for outputting the detection signal DET corresponding to the concentration of the chemicals CHM and a calibration mode for calibrating the gas sensor 100. The calibrator 122 may generate the calibration data CAL based on the frequency signal FRQ in the calibration mode. The calibration data CAL may include information for compensating for a change in the characteristics of the gas sensing device 110, and may be used by the compensator 123 in the sensing mode. As described below with reference to FIG. 5 and the like, in some example embodiments, the calibrator 122 may generate the calibration data CAL based on the resonant frequency of a heated gas sensing device 110 (e.g., based on the frequency of the output signal OSC), in the calibration mode. Furthermore, in some example embodiments, the calibrator 122 may determine whether to generate the calibration data CAL when entering the calibration mode. In some example embodiments, unlike the case shown in FIG. 1, the calibrator 122 may receive the detection signal DET generated by the compensator 123 instead of the frequency signal FRQ generated by the frequency detector 121, or may receive both the frequency signal FRQ and the detection signal DET. An example of the operation of the calibrator 122 is described below with reference to FIG. 5 and the like.

The compensator 123 may receive the frequency signal FRQ from the frequency detector 121 and may receive the calibration data CAL from the calibrator 122. The compensator 123 may generate the detection signal DET by adjusting the frequency signal FRQ based on the calibration data CAL in the sensing mode. For example, the compensator 123 may include an adder, and may add a frequency offset contained in the calibration data CAL to a frequency represented by the frequency signal FRQ. In some example embodiments, the compensator 123 may further adjust the frequency signal FRQ according to initial calibration data (e.g., CAL0 in FIG. 7) obtained by calibrating the gas sensor 100 during the manufacturing of the gas sensor 100.

Figure 2A:
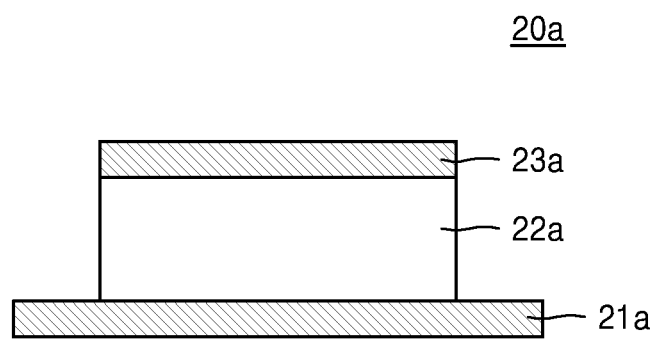
FIGS. 2A and 2B are views illustrating examples of a gas sensing device in FIG. 1, according to some example embodiments.
Figure 2B:
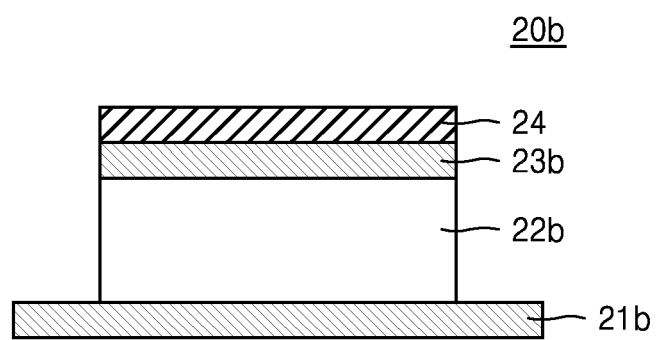

FIGS. 2A and 2B are views illustrating examples of the gas sensing device 110 in FIG. 1, according to some example embodiments. For example, FIG. 2A illustrates an FBAR 20a as an example of a resonator included in the gas sensing device 110, and FIG. 2B illustrates an FBAR sensor 20b including an FBAR. In some example embodiments, the gas sensing device 110 of FIG. 1 may further include the FBAR sensor 20b of FIG. 2B and a drive circuit for driving the FBAR sensor 20b. Hereinafter, the features or elements of FIGS. 2A and 2B, which are the same as those described above, are omitted.

Referring to FIG. 2A, the FBAR 20a may have a structure in which a lower electrode 21a, a piezoelectric layer 22a, and an upper electrode 23a are sequentially stacked. The piezoelectric layer 22a may be formed in a thin film form, and may include zinc oxide (ZnO), aluminum nitride (AlN), lead zirconate titanate (PZT), or any other piezoelectric material. The resonant frequency of the FBAR 20a may be determined by the thickness of the piezoelectric layer 22a, and when a voltage is applied to the lower electrode 21a and the upper electrode 23a, the FBAR 20a may be resonated in parallel with a direction in which the lower and upper electrodes 21a and 23a and the piezoelectric layer 22a are stacked. In some example embodiments, the FBAR 20a may be formed on a substrate including silicon or glass, and an insulating layer including $SiO_2$ or the like may be located between the FBAR 20a and the substrate.

Referring to FIG. 2B, the FBAR sensor 20b may include a lower electrode 21b, a piezoelectric layer 22b, and an upper electrode 23b, which constitute an FBAR and are sequentially stacked. The FBAR sensor 20b may further include a sensing layer 24 on the upper electrode 23b. The sensing layer 24 may be coated on the FBAR to sense gas. When chemicals CHM are adsorbed to the sensing layer 24, the resonant frequency of the FBAR may be changed and the concentration of the chemicals CHM may be detected by detecting a change in the resonant frequency of the FBAR. Accordingly, a heater or the like for gas detection may be omitted, and the FBAR sensor 20b may be manufactured by a semiconductor process and thus may be downsized. The sensing material of the sensing layer 24 may be determined by the chemicals CHM to be sensed. In some example embodiments, the sensing layer 24 may include a polymer or may include a polymer for different chemicals CHM to be sensed.

When the sensing layer 24 is heated, the molecular weight of the chemicals CHM desorbed from the sensing layer 24 due to molecular activity activated at high temperature may increase and thus the sensitivity of the FBAR sensor 20b may be reduced. When the temperature of the FBAR sensor 20b is raised to a certain temperature (e.g., $T_{CAL}$ in FIG. 4) or more, the FBAR sensor 20b may have a resonant frequency independent of the chemicals CHM. In this case, the calibrator 122 of FIG. 1 may detect the degree of change in the characteristics of the gas sensing device 110 based on the resonant frequency of the heated gas sensing device 110 in a calibration mode.

Figure 3A:
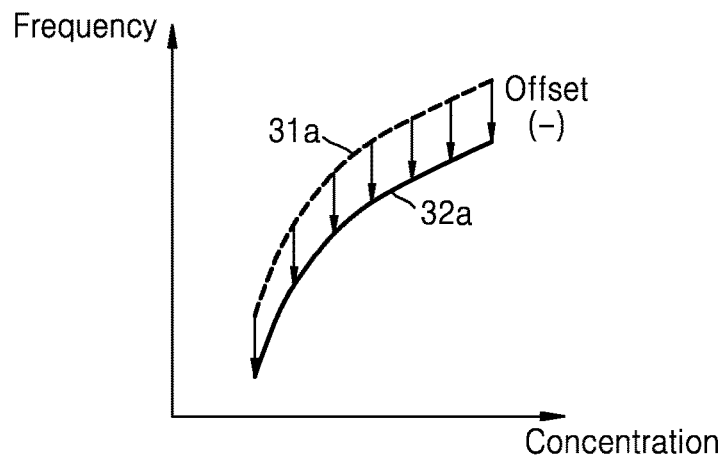
FIGS. 3A and 3B are graphs showing changes in the characteristics of the gas sensing device of FIG. 1, according to some example embodiments.
Figure 3B:
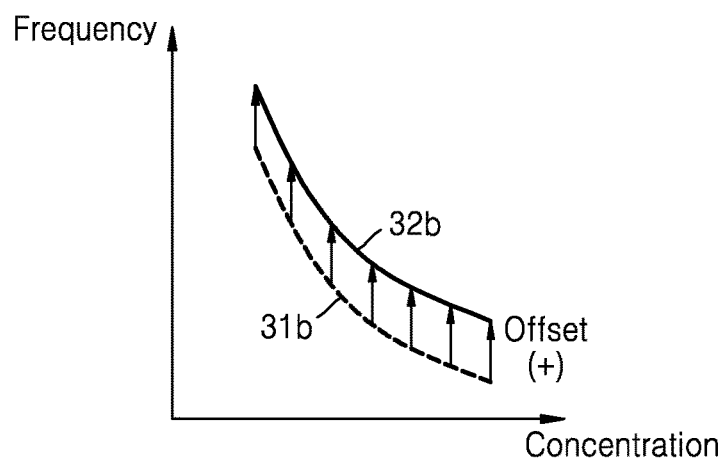

FIGS. 3A and 3B are graphs showing changes in the characteristics of the gas sensing device 110 in FIG. 1, according to some example embodiments. For example, FIG. 3A illustrates an example of a gas sensing device 110 having a resonant frequency proportional to the concentration of the chemicals CHM. FIG. 3B illustrates an example of a gas sensing device 110 having a resonant frequency inversely proportional to the concentration of the chemicals CHM. Hereinafter, FIGS. 3A and 3B are described with reference to FIG. 1.

Referring to FIG. 3A, the gas sensing device 110 may have a resonant frequency that increases as the concentration of the chemicals CHM increases. The gas sensing device 110 may have a concentration-frequency characteristic curve 31a as indicated by a dashed line, at the beginning (e.g., at the time of manufacturing the gas sensor 100), and then due to various causes, the gas sensing device 110 may have a concentration-frequency characteristic curve 32a as indicated by a solid line. In some example embodiments, the concentration-frequency characteristic curve 32a may have a negative frequency offset from the concentration-frequency characteristic curve 31a, as shown in FIG. 3A. In some example embodiments, a changed concentration-frequency characteristic of the gas sensing device 110 may correspond to a concentration-frequency characteristic curve having a positive frequency offset from the concentration-frequency characteristic curve 31a, unlike the case shown in FIG. 3A.

Referring to FIG. 3B, the gas sensing device 110 may have a resonant frequency that decreases as the concentration of the chemicals CHM increases. The gas sensing device 110 may have a concentration-frequency characteristic curve 31b as indicated by a dashed line, at the beginning (e.g., at the time of manufacturing the gas sensor 100), and then due to various causes, the gas sensing device 110 may have a concentration-frequency characteristic curve 32b as indicated by a solid line. In some example embodiments, the curve 32b may have a positive frequency offset from the concentration-frequency characteristic curve 31b, as shown in FIG. 3B. In some example embodiments, a changed concentration-frequency characteristic of the gas sensing device 110 may correspond to a concentration-frequency characteristic curve having a negative frequency offset from the concentration-frequency characteristic curve 31b, unlike the case shown in FIG. 3B.

As described above with reference to FIGS. 3A and 3B, a frequency offset may occur in the relationship of the characteristics of the gas sensing device 110 (e.g., the concentration of the chemicals CHM and the resonant frequency). The accuracy of the gas sensor 100 may be reduced due to the frequency offset. However, the calibrator 122 of FIG. 1 may accurately detect the frequency offset regardless of the concentration of the chemicals CHM in a calibration mode and may generate calibration data CAL including the detected frequency offset. The compensator 123 may accurately compensate for a change in the characteristics of the gas sensing device 110 by adding the frequency offset included in the calibration data CAL in a sensing mode.

Figure 4:
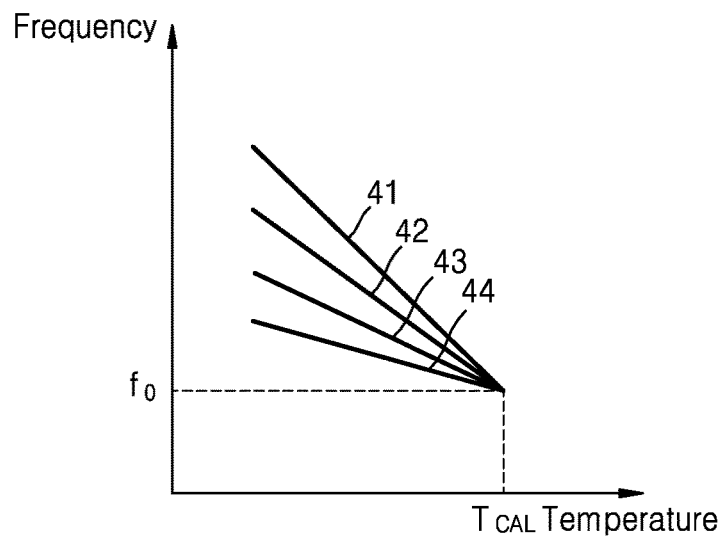
FIG. 4 is a graph showing the characteristics of the gas sensing device in FIG. 1, according to an example embodiment.

FIG. 4 is a graph showing the characteristics of the gas sensing device 110 in FIG. 1, according to an example embodiment. For example, FIG. 4 is a graph showing the relationship between the temperature of the gas sensing device 110 and the resonant frequency thereof. In FIG. 4, straight lines 41 to 44 may correspond to different concentrations of the chemicals CHM, respectively. Although the temperature-frequency characteristic of the gas sensing device 110 is shown as having linearity in FIG. 4, the temperature-frequency characteristic may correspond to a curve, unlike the case shown in FIG. 4.

Referring to FIG. 4, the gas sensing device 110 may have a resonant frequency that decreases as the temperature rises. That is, as described above with reference to FIG. 2B, due to active molecular motion at high temperature, the molecular weight of chemicals CHM desorbed from the sensing layer 24 relative to the molecular weight of chemicals CHM adsorbed to the sensing layer 24 may increase, and thus the resonant frequency may decrease. As shown in FIG. 4, the gas sensing device 110 may have different resonant frequencies due to different concentrations of the chemicals CHM at relatively low temperature. Further, differences between resonant frequencies corresponding to the different concentrations of the chemicals CHM may be reduced, and the gas sensing device 110 may have approximately the same resonant frequency $f_0$ at a particular high temperature (i.e. $T_{CAL}$) in spite of the different concentrations of the chemicals CHM. In the present specification, a temperature at which the gas sensing device 110 has a resonant frequency $f_0$ that is approximately constant independently of the concentration (or gas concentration) of the chemicals CHM may be referred to as a calibration temperature $T_{CAL}$.

The gas sensing device 110 heated to the calibration temperature $T_{CAL}$ may have a resonant frequency that depends on its changed characteristics regardless of the concentration of the chemicals CHM, and as described below, the calibrator 122 may detect a frequency offset based on the amount of change of the resonant frequency at the calibration temperature $T_{CAL}$. In some example embodiments, the calibration temperature $T_{CAL}$ may be fixed during the manufacturing of the gas sensor 100, and in some example embodiments, the calibration temperature $T_{CAL}$ may be set by the calibrator 122 from one or more factors. In some example embodiments, the calibration temperature $T_{CAL}$ may be less than a heat treatment temperature (e.g., about 300° C.) for a polymer included in the sensing layer 24 of FIG. 2B, and may be, for example, between about 80° C. and about 100° C.

Figure 5:
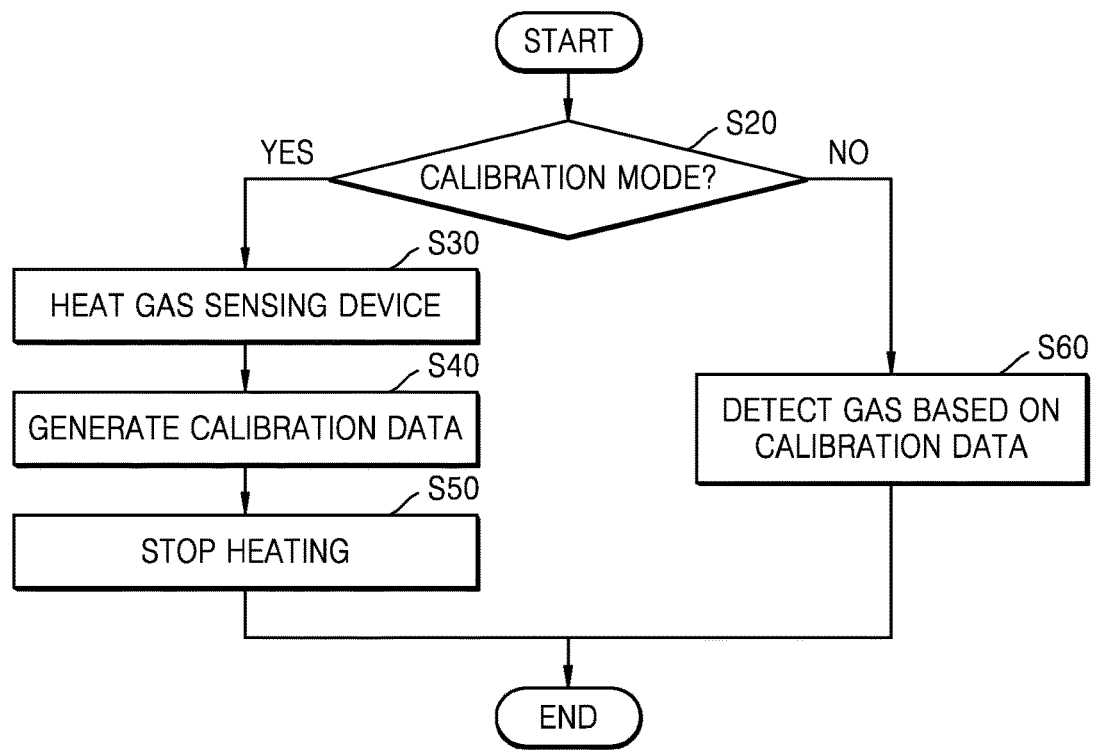
FIG. 5 is a flowchart of a method of calibrating a gas sensor, according to an example embodiment.

FIG. 5 is a flowchart of a method of calibrating a gas sensor, according to an example embodiment. For example, the method of FIG. 5 may be repeatedly performed by the gas sensor 100 of FIG. 1. Hereinafter, FIG. 5 is described with reference to FIGS. 1 and 4.

In operation S20, an operation of determining whether to enter a calibration mode may be performed. In some example embodiments, the gas sensor 100 may enter the calibration mode at each desired (or alternatively, predefined) period, and it may be determined in operation S20 whether the desired (or alternatively, predefined) period for entering the calibration mode has been reached. In some example embodiments, the calibration mode may be triggered by an input received from the outside of an apparatus including the gas sensor 100, for example, by a user of the apparatus, and it may be determined in operation S20 whether or not an input has been received. In some example embodiments, the gas sensor 100 may enter the calibration mode based on the detection signal DET. For example, when the concentration of the chemicals CHM corresponding to the detection signal DET is equal to or greater than a reference value for a certain time or more or is less than the reference value for a certain time or more, the gas sensor 100 may enter the calibration mode. In some example embodiments, the gas sensor 100 may enter the calibration mode in response to a power supply. As shown in FIG. 5, when it is determined that the gas sensor 100 has entered the calibration mode, operation S30 may be subsequently performed, whereas when it is determined that the gas sensor 100 has not entered the calibration mode (e.g., when it is determined that the gas sensor 100 is still in a sensing mode), operation S60 may be subsequently performed.

When it is determined that the gas sensor 100 has entered the calibration mode, an operation of heating the gas sensing device 110 may be performed in operation S30. For example, the calibrator 122 may heat the gas sensing device 110 by turning on a heater. In some example embodiments, the heater for heating the gas sensing device 110 may be provided outside the gas sensor. In some example embodiments, the heater for heating the gas sensing device 110 may be included in the gas sensor 100, as described below with reference to FIG. 12. The gas sensing device 110 may be heated until the calibration temperature $T_{CAL}$ is reached and thus may have the resonant frequency $f_0$ that is independent of the concentration of the chemicals CHM. In some example embodiments, the calibration temperature $T_{CAL}$ may be set dynamically, as described below with reference to FIG. 11.

In operation S40, an operation of generating the calibration data CAL may be performed. For example, the calibrator 122 may receive the frequency signal FRQ generated by the frequency detector 121 from the output signal OSC, which has been generated by the gas sensing device 110 that has been heated to the calibration temperature $T_{CAL}$, and may obtain the resonant frequency $f_0$ in terms of, for example, the obtained frequency signal FRQ. The calibrator 122 may detect the characteristics of the gas sensing device 110 based on the obtained resonant frequency $f_0$ and may generate the calibration data CAL based on the detected characteristics of the gas sensing device 110. An example of operation S40 is described below with reference to FIG. 9.

In operation S50, an operation of stopping the heating may be performed. For example, the calibrator 122 may stop heating of the gas sensing device 110 by turning off the heater after the calibration data CAL is generated in operation S40. In some example embodiments, the calibrator 122 may wait for a certain amount of time until the gas sensing device 110 reaches an ambient temperature, e.g., the room temperature, after the heating is stopped.

When it is determined that the gas sensor 100 has not entered the calibration mode in operation S20, an operation of detecting gas taking into account the calibration data CAL may be performed in operation S60. For example, the compensator 123 may generate the detection signal DET by adjusting the frequency signal FRQ generated by the frequency detector 121 based on the calibration data CAL generated in operation S40. An example of operation S60 is described below with reference to FIG. 9.

Figure 6:
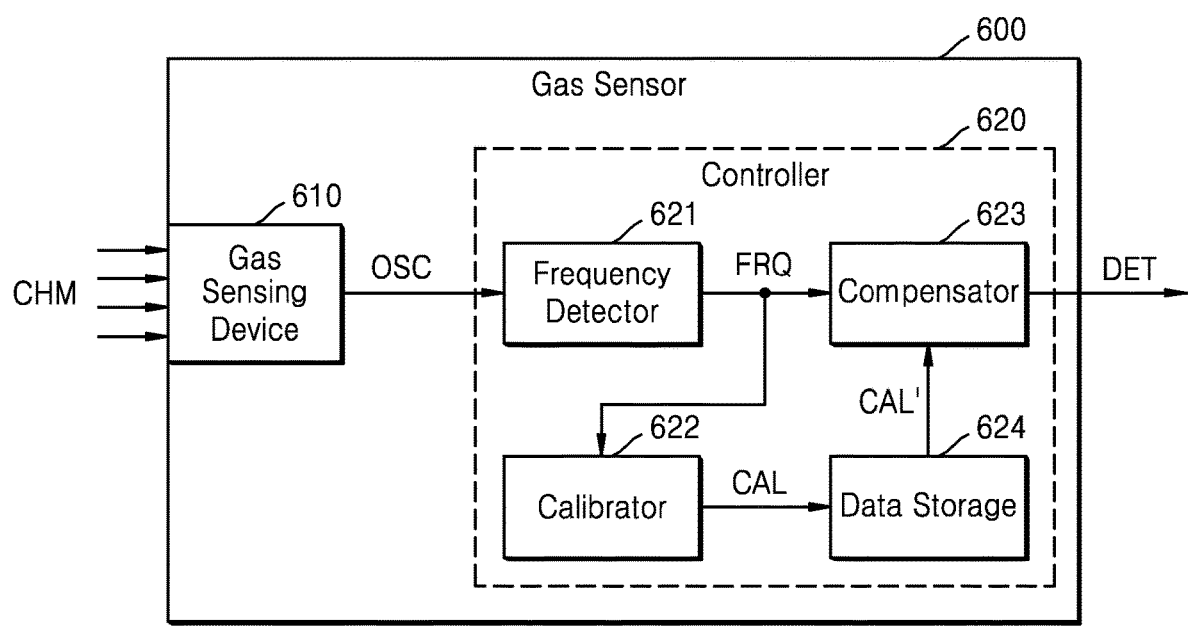
FIG. 6 is a block diagram of a gas sensor according to an example embodiment.

FIG. 6 is a block diagram of a gas sensor 600 according to an example embodiment.

As shown in FIG. 6, the gas sensor 600 may include a gas sensing device 610 and a controller 620. Hereinafter, the features or elements of FIG. 6, which are the same as those of FIG. 1, are omitted.

The controller 620 may include a frequency detector 621, a calibrator 622, a compensator 623, and a data storage 624. The controller 620 of FIG. 6 may further include the data storage 624, as compared to the controller 120 of FIG. 1. The frequency detector 621 may generate a frequency signal FRQ by detecting the frequency of an output signal OSC of the gas sensing device 610. The frequency signal FRQ may be provided to the calibrator 622 and the compensator 623. The calibrator 622 may generate calibration data CAL based on the frequency signal FRQ in a calibration mode, and may store the calibration data CAL in the data storage 624. The compensator 623 may receive calibration data CAL' from the data storage 624, and may generate a detection signal DET by compensating for the frequency signal FRQ based on the calibration data CAL'.

The data storage 624 may include, but is not limited to, a non-volatile memory device (e.g., electrically erasable programmable read-only memory (EEPROM), a flash memory, phase change random access memory (PRAM), resistance random access memory (RRAM), nano floating gate memory (NFGM), polymer random access memory (PoRAM), magnetic random access memory (MRAM), and ferroelectric random access memory (FRAM)), or may include a volatile memory device (e.g., dynamic random access memory (DRAM), static random access memory (SRAM), a mobile DRAM, double data rate synchronous dynamic random access memory (DDR SDRAM), low power DDR (LPDDR) SDRAM, graphic DDR (GDDR) SDRAM, and Rambus dynamic random access memory (RDRAM)). The data storage 624 may store the calibration data CAL received from the calibrator 622 in the calibration mode, and may provide stored calibration data CAL' to the compensator 623 in a sensing mode. As described below with reference to FIG. 7, the data storage 624 may further store additional data for calibration and/or compensation, as well as the calibration data CAL provided by the calibrator 622. An example of the data storage 624 is described below with reference to FIG. 7.

Figure 7:
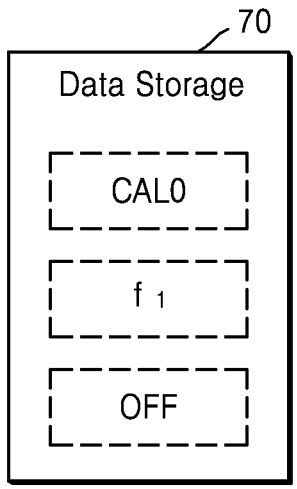
FIG. 7 is a block diagram illustrating an example of a data storage in FIG. 6, according to an example embodiment.

FIG. 7 is a block diagram illustrating an example of the data storage 624 in FIG. 6, according to an example embodiment. As described above with reference to FIG. 6, a data storage 70 of FIG. 7 may receive and store the calibration data CAL from the calibrator 622, and may provide the stored calibration data CAL' to the compensator 623. As shown in FIG. 7, the data storage 70 may store initial calibration data CAL0, a first resonant frequency and a frequency offset OFF. In some example embodiments, unlike the case shown in FIG. 7, the data storage 70 may be configured such that the initial calibration data CAL0, the first resonant frequency $f_1$, and the frequency offset OFF are stored in different types of memory devices, respectively. For example, the initial calibration data CAL0 and the first resonant frequency $f_1$ may be stored in a non-volatile memory device, whereas the frequency offset OFF may be stored in a volatile memory device. Hereinafter, FIG. 7 is described with reference to FIG. 6.

The initial calibration data CAL0 may be generated, for example, at the time of manufacturing the gas sensor 600 and stored in the data storage 70. For example, the gas sensing device 610 may have process variations, and the initial calibration data CAL0 may include information to compensate for the process variations. The compensator 623 may adjust the frequency signal FRQ based on the initial calibration data CAL0 in the sensing mode.

The first resonant frequency $f_1$ may refer to a resonant frequency of the gas sensing device 610 at the calibration temperature $T_{CAL}$ at the time of manufacturing the gas sensor 600. The first resonant frequency $f_1$ may be determined independently of the concentration of the chemicals CHM due to the calibration temperature $T_{CAL}$, and then may be compared to a resonant frequency (e.g., the second resonant frequency $f_2$ of FIG. 10) detected during a calibration operation. The data storage 70 may store a frequency offset OFF corresponding to a difference between the first and second resonant frequencies $f_1$ and $f_2$. For example, the calibrator 622 may obtain the first resonant frequency $f_1$ from the data storage 70 in the calibration mode, and may generate the frequency offset OFF as calibration data based on a resonant frequency obtained from the frequency signal FRQ and the first resonant frequency $f_1$ and store the generated frequency offset OFF in the data storage 70.

Figure 8:
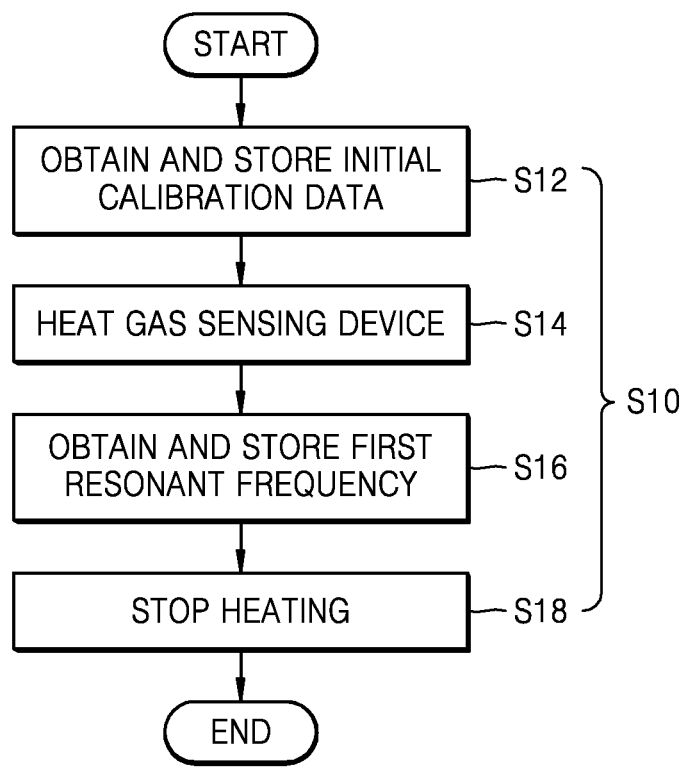
FIG. 8 is a flowchart of a method of calibrating a gas sensor, according to an example embodiment.

FIG. 8 is a flowchart of a method of calibrating a gas sensor, according to an example embodiment. For example, in operation S10 of FIG. 8, the initial calibration data CAL0 and the first resonant frequency $f_1$ of FIG. 7 may be obtained. In some example embodiments, operation S10 may be performed during the manufacturing of the gas sensor 600 of FIG. 6, for example, before operation S20 of FIG. 5. As shown in FIG. 8, operation S10 may include operations S12, S14, S16, and S18. FIG. 8 is described with reference to FIG. 6.

In operation S12, an operation of obtaining and storing initial calibration data CAL0 may be performed. For example, the gas sensor 600 may be fabricated by a semiconductor process, and the gas sensing device 610 included in the gas sensor 600 may have process variations although the gas sensor 600 is fabricated in the same semiconductor process. A test apparatus may detect the characteristics of the gas sensing device 610 by testing the gas sensor 600, and may generate the initial calibration data CAL0 for calibrating the process variations based on the detected characteristics. For example, the gas sensing device 610 may have a resonant frequency different from a reference resonant frequency at a desired (or alternatively, predefined) temperature and gas concentration, and the initial calibration data CAL0 may include calibration values such that the gas sensor 600 outputs a detection signal DET corresponding to the reference resonant frequency. The calibration values in the initial calibration data CAL0 may be used to adjust the frequency signal FRQ by the compensator 623 while the gas sensor 600 senses gas in the sensing mode. The gas sensor 600 may receive the initial calibration data CAL0 from the test apparatus, and store the received initial calibration data CAL0 in the data storage 624.

In operation S14, an operation of heating the gas sensing device 610 may be performed. For example, as described above with reference to FIG. 5, the calibrator 622 may heat the gas sensing device 610 by turning on a heater to form the same condition as the calibration mode, and the gas sensing device 610 may be heated until the calibration temperature $T_{CAL}$ is reached.

In operation S16, an operation of obtaining and storing a first resonant frequency $f_1$ may be performed. As described above with reference to FIG. 7, the first resonant frequency $f_1$ may correspond to a resonant frequency of the gas sensing device 610 regardless of the concentration of the chemicals CHM at the calibration temperature MAL. The calibrator 622 may obtain a first resonant frequency $f_1$ based on the frequency signal FRQ, and may store the first resonant frequency $f_1$ in the data storage 624. The first resonant frequency $f_1$ stored in the data storage 624 may be used by the calibrator 622 in the calibration mode, as described below with reference to FIG. 9.

In operation S18, an operation of stopping the heating may be performed. For example, the calibrator 622 may stop heating to the gas sensing device 610 by turning off the heater after the first resonant frequency $f_1$ is stored in operation S16. In some example embodiments, operations S14, S16, and S18 may be performed by making the gas sensor 600 enter the calibration mode arbitrarily at the time of manufacturing the gas sensor 600.

Figure 9:
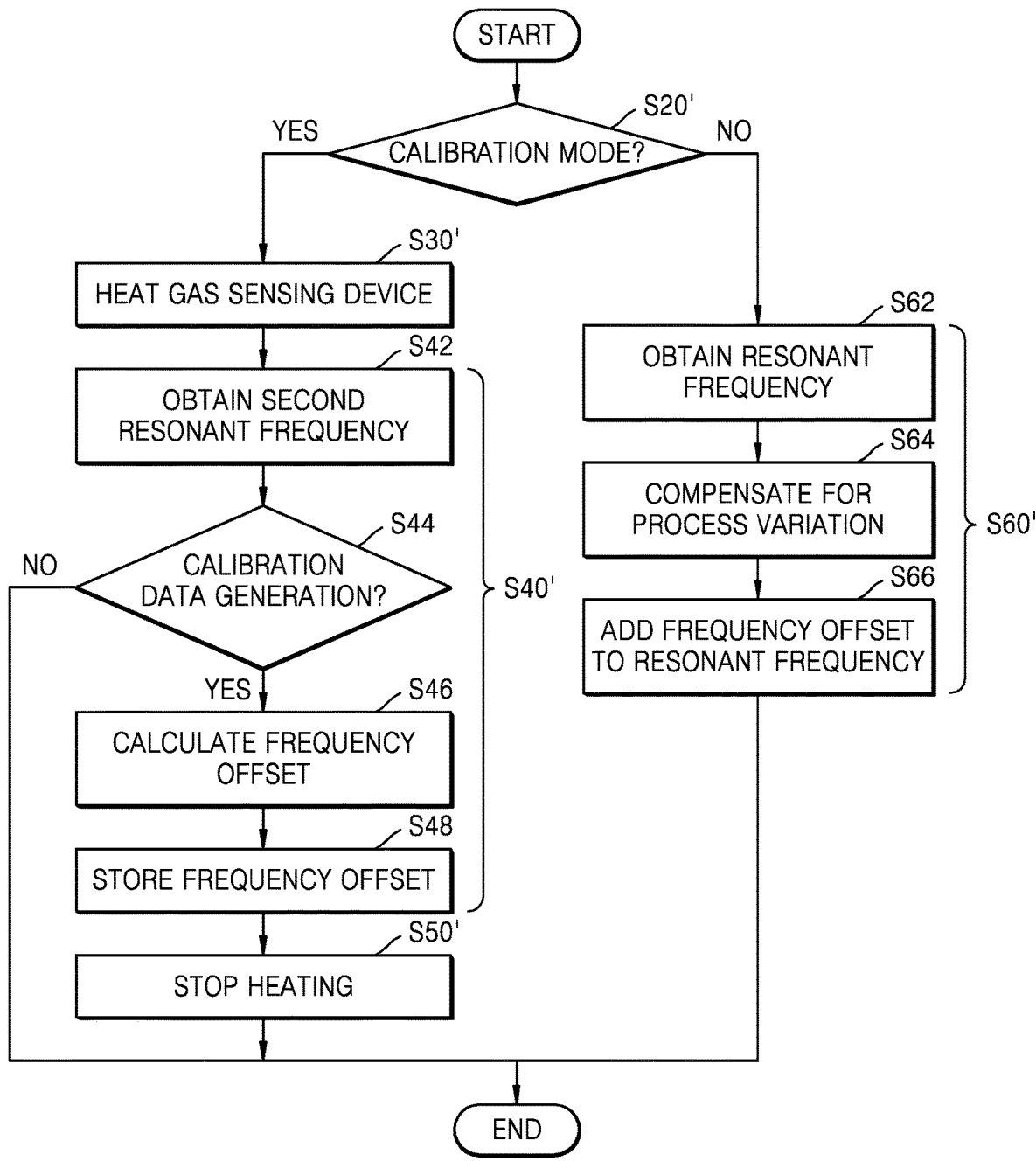
FIG. 9 is a flowchart of a method of calibrating a gas sensor, according to an example embodiment.
Figure 10:
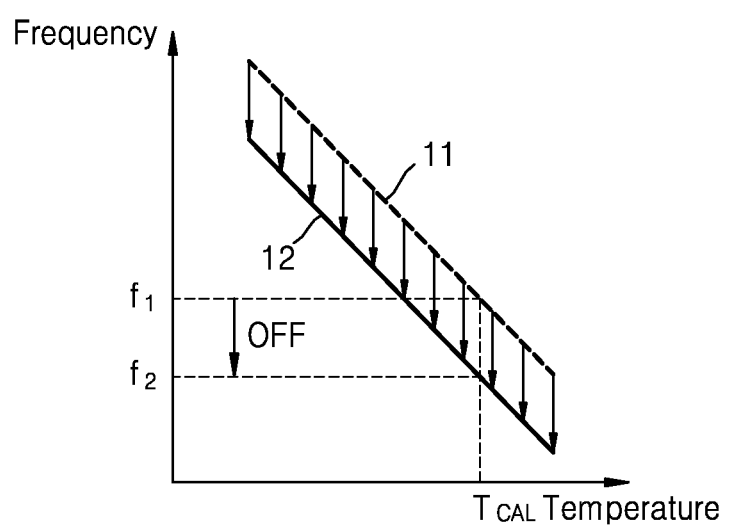
FIG. 10 is a graph showing a temperature-frequency characteristic of a gas sensing device at a constant gas concentration, according to an example embodiment.

FIG. 9 is a flowchart of a method of calibrating a gas sensor, according to an example embodiment, and FIG. 10 is a graph showing a temperature-frequency characteristic of a gas sensing device at a constant gas concentration, according to an example embodiment. For example, the method of FIG. 9 may be repeatedly performed by the gas sensor 600 of FIG. 6. Hereinafter, FIGS. 9 and 10 are described with reference to FIG. 6. The features or elements of FIG. 9, which are the same as those of FIG. 5, are omitted.

In operation S20', an operation of determining whether or not the gas sensor 600 has entered a calibration mode may be performed. As shown in FIG. 9, when it is determined that the gas sensor 600 has entered the calibration mode, operation S30' may be subsequently performed, whereas when it is determined that the gas sensor 600 is maintained in a sensing mode, operation S60' may be subsequently performed.

When it is determined that the gas sensor 600 has entered the calibration mode, an operation of heating the gas sensing device 610 may be performed in operation S30'. For example, the calibrator 622 may heat the gas sensing device 610 by turning on a heater, and the gas sensing device 610 may be heated until the calibration temperature $T_{CAL}$ is reached.

In operation S40', similar to operation S40 of FIG. 5, an operation of generating calibration data CAL may be performed. For example, the calibrator 622 may generate a frequency offset OFF as the calibration data CAL. As shown in FIG. 9, operation S40' may include operation S42, operation S44, operation S46, and operation S48.

In operation S42, an operation of obtaining a second resonant frequency $f_2$ may be performed. The second resonant frequency $f_2$ may refer to a resonant frequency of the gas sensing device 610 at the calibration temperature $T_{CAL}$. As shown by the dashed line 11 in FIG. 10, the gas sensing device 610 may have a first resonant frequency $f_1$ at the calibration temperature $T_{CAL}$ during the manufacturing of the gas sensor 600, whereas due to a changed temperature-frequency characteristic of the gas sensing device 610, as shown by the solid line 12 in FIG. 10, the gas sensing device 610 may have the second resonant frequency $f_2$ at the calibration temperature $T_{CAL}$ in the current calibration mode. In some example embodiments, unlike the case shown in FIG. 10, the second resonant frequency $f_2$ may be greater than the first resonant frequency $f_1$. The calibrator 622 may obtain the second resonant frequency $f_2$ based on the frequency signal FRQ.

In operation S44, an operation of determining whether to generate the calibration data CAL may be performed. For example, the calibrator 622 may generate the calibration data CAL only when the characteristic change of the gas sensing device 610 is greater than a certain level. In some example embodiments, the calibrator 622 may determine whether to generate the calibration data CAL based on the first resonant frequency $f_1$ and the second resonant frequency $f_2$. For example, the calibrator 622 may generate the calibration data CAL when the ratio of the second resonant frequency $f_2$ to the first resonant frequency $f_1$ exceeds a reference value. In some example embodiments, when Equation 1 is satisfied, the calibrator 622 may determine to generate the calibration data CAL.

$$\frac{|f_2 - f_1|}{f_1} > r \qquad \text{[Equation 1]}$$

In Equation 1, r is a positive real number, which may be a desired (or alternatively, predefined) fixed value or may be a value adaptively adjusted by the calibrator 622 based on repeatedly detected values of the second resonant frequency $f_2$. When it is determined to generate the calibration data CAL in operation S44 (YES), operation S46 may be subsequently performed. When it is determined not to generate the calibration data CAL in operation S44 (NO), the method of FIG. 9 may be ended and then operation S20' may be performed again.

In operation S46, an operation of calculating a frequency offset OFF may be performed. For example, the calibrator 622 may calculate the frequency offset OFF based on the first resonant frequency $f_1$ and the second resonant frequency $f_2$. For example, the calibrator 622 may calculate the frequency offset OFF according to Equation 2.

$$\text{OFF} = f_2 - f_1 \qquad \text{[Equation 2]}$$

The frequency offset OFF may have a negative value, as shown in FIG. 10, or may have a positive value, unlike the case shown in FIG. 10.

In operation S48, an operation of storing the frequency offset OFF may be performed. For example, the calibrator 622 may store the frequency offset OFF calculated in operation S46 in the data storage 624 as calibration data CAL. In some example embodiments, in operation S20', the gas sensor 600 may enter the calibration mode in response to a power supply, and the calibrator 622 may generate a frequency offset OFF and store the generated frequency offset OFF in a volatile memory device.

In operation S50', an operation of stopping the heating may be performed. For example, the calibrator 622 may stop heating to the gas sensing device 610 by turning off the heater, and the gas sensing device 610 may reach an ambient temperature, e.g., room temperature.

When it is determined in operation S20' that the gas sensor 600 has not entered the calibration mode, an operation of detecting gas based on the calibration data CAL may be performed in operation S60', similar to operation S60 in FIG. 5. As shown in FIG. 9, operation S60' may include operations S62, S64, and S66.

In operation S62, an operation of obtaining a resonant frequency may be performed. For example, the compensator 623 may obtain the resonant frequency of the gas sensing device 610 based on the frequency signal FRQ generated by the frequency detector 621. The resonant frequency may depend not only on the concentration of the chemicals CHM but also on the process variation and characteristic change of the gas sensing device 610.

In operation S64, an operation of compensating for the process variation may be performed. For example, the compensator 623 may read initial calibration data CAL0 from the data storage 624 and may compensate for the process variation of the gas sensing device 610 based on the initial calibration data CAL0.

In operation S66, an operation of adding the frequency offset OFF to the resonant frequency may be performed. For example, the compensator 623 may read the frequency offset OFF from the data storage 624 and add the frequency offset OFF to the resonant frequency where the process variation is compensated for. Accordingly, the calibration data CAL generated in the calibration mode may be reflected, and the compensator 623 may generate a detection signal DET which corresponds to the current gas concentration with improved precision.

Figure 11:
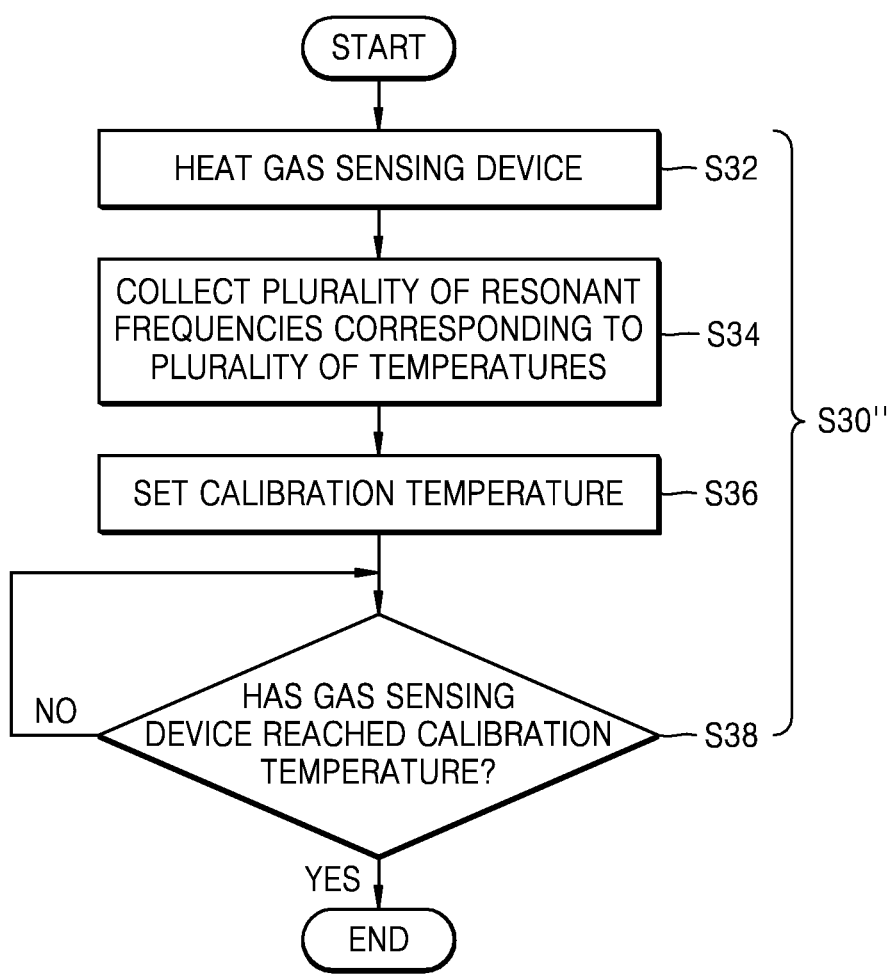
FIG. 11 is a flowchart illustrating an example of operation S30 in FIG. 5, according to an example embodiment.

FIG. 11 is a flowchart illustrating an example of operation S30 in FIG. 5, according to an example embodiment. An operation of heating a gas sensing device (e.g., the gas sensing device 110 in FIG. 1) may be performed in operation S30" of FIG. 11, as in operation S30 of FIG. 5 and operation S30' of FIG. 9. For example, the calibration temperature $T_{CAL}$ may be dynamically set in operation S30" of FIG. 11. As shown in FIG. 11, operation S30" may include operation S32, operation S34, operation S36, and operation S38. Hereinafter, FIG. 11 is described with reference to FIGS. 1 and 5.

When it is determined in operation S20 of FIG. 5 or operation S20' of FIG. 9 that the gas sensor 600 has entered the calibration mode, operation S30" may be subsequently performed. In operation S32, an operation of heating the gas sensing device 110 may be performed. For example, the calibrator 122 may heat the gas sensing device 110 by turning on a heater.

In operation S34, an operation of collecting a plurality of resonant frequencies corresponding to a plurality of temperatures may be performed. For example, the calibrator 622 may collect a plurality of resonant frequencies of the gas sensing device 610 at each of a plurality of desired (or alternatively, predefined) temperatures in a process in which the temperature of the gas sensing device 610 heated in operation S32 rises. Because the plurality of resonant frequencies are collected at dense points in time, the plurality of resonant frequencies may correspond to the same or substantially similar gas concentration. Thus, a curve corresponding to the current temperature-frequency characteristic of the gas sensing device 610 may be obtained. For example, as described above with reference to FIG. 4, the temperature-frequency characteristic of the gas sensing device 610 may correspond to different straight lines 41 to 44 depending on the gas concentration. However, the plurality of resonant frequencies collected in operation S34 may be on one of the straight lines 41 to 44 of FIG. 4, and thus, in a graph of temperature and resonant frequency, a drifted straight line may be obtained due to a change in the temperature-frequency characteristic of the gas sensing device 610. In some example embodiments, the gas sensing device 610 may have a temperature-frequency characteristic corresponding to a curve instead of a straight line in the graph of temperature and resonant frequency, and also in this case, a drifted curve may be obtained due to a change in the temperature-frequency characteristic of the gas sensing device 610 from the plurality of resonant frequencies collected in operation S34.

In operation S36, an operation of setting the calibration temperature $T_{CAL}$ may be performed. The temperature-frequency characteristic of the gas sensing device 610 may be obtained according to the plurality of resonant frequencies collected in operation S34, and the calibration temperature $T_{CAL}$ may be determined based on the temperature-frequency characteristic. For example, the calibrator 122 may obtain a curve corresponding to the temperature-frequency characteristic of the gas sensing device 610 based on the plurality of resonant frequencies, and may determine the calibration temperature $T_{CAL}$ based on the slope of the curve. Then, the calibrator 122 may set the determined calibration temperature $T_{CAL}$ as a calibration temperature to use in the current calibration mode.

In operation S38, an operation of determining whether the gas sensing device 110 has reached the calibration temperature $T_{CAL}$ may be performed. When it is determined that the gas sensing device 110 has not reached the calibration temperature $T_{CAL}$, operation S38 may be repeatedly performed. When it is determined that the gas sensing device 110 has reached the calibration temperature $T_{CAL}$, operation S38 may be ended and operation S40 of FIG. 5 or operation S40' of FIG. 9 may be subsequently performed.

Figure 12:
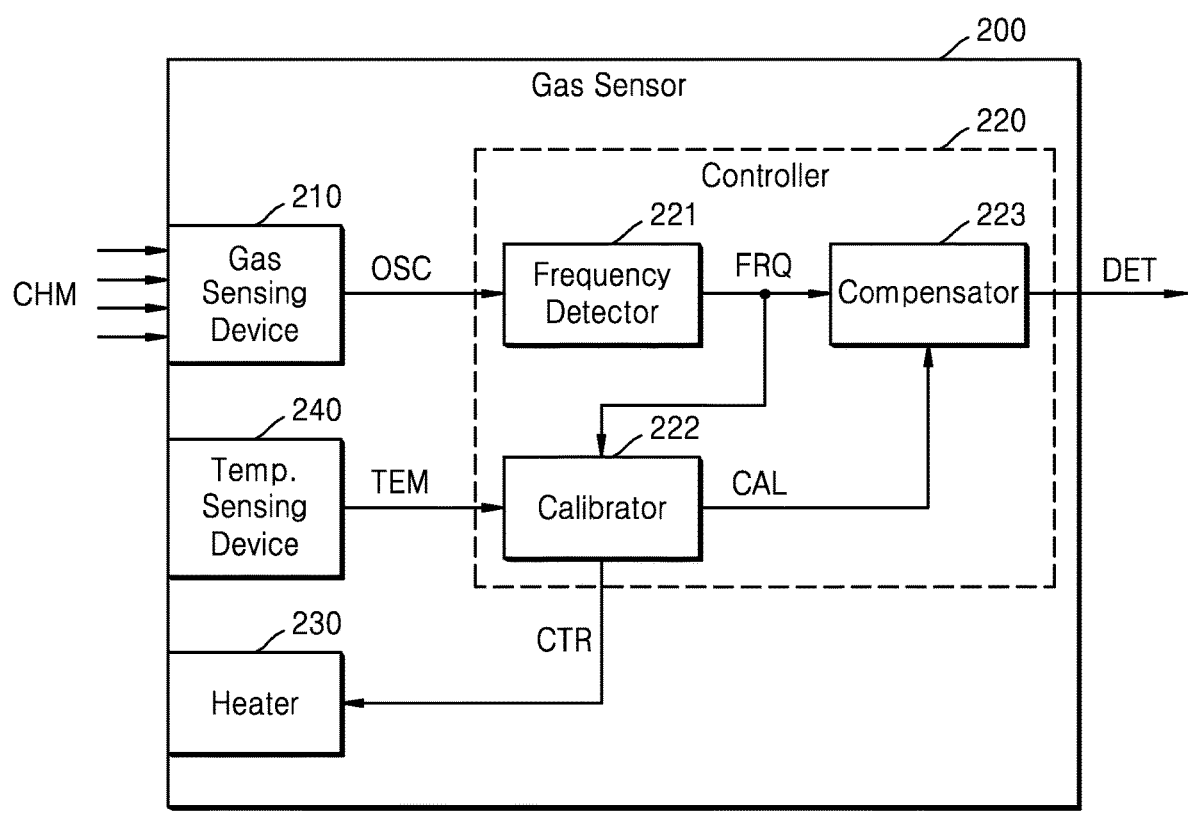
FIG. 12 is a block diagram of a gas sensor according to an example embodiment.

FIG. 12 is a block diagram of a gas sensor 200 according to an example embodiment.

As shown in FIG. 12, the gas sensor 200 may include a gas sensing device 210, a controller 220, a heater 230, and a temperature sensing device 240. Compared to the gas sensor 100 of FIG. 1, the gas sensor 200 of FIG. 12 may further include the heater 230 and the temperature sensing device 240, which communicate with a calibrator 222 of the controller 220. In some example embodiments, unlike the case shown in FIG. 12, the gas sensor 200 may include one of the temperature sensing device 240 or the heater 230, the other one of the temperature sensing device 240 or the heater 230 may be provided outside the gas sensor 200. In such case, and the calibrator 222 may communicate with the other one of the temperature sensing device 240 or the heater 230. Hereinafter, the features or elements of FIG. 12, which are the same as those of FIG. 1, are omitted.

The gas sensing device 210 may generate an output signal OSC having a frequency that varies according to chemicals CHM, and the controller 220 may generate a detection signal DET corresponding to the concentration of the chemicals CHM based on the output signal OSC. The controller 220 may include a frequency detector 221, a calibrator 222, and a compensator 223. The controller 220 may further include a data storage (e.g., the data storage 624 in FIG. 6). The frequency detector 221 may generate a frequency signal FRQ corresponding to the frequency of the output signal OSC, the calibrator 222 may generate calibration data CAL based on the frequency signal FRQ in a calibration mode, and the compensator 223 may generate the detection signal DET by adjusting the frequency signal FRQ based on the calibration data CAL in a sensing mode.

The heater 230 may heat the gas sensing device 210 in response to a control signal CTR received from the calibrator 222. The heater 230 may have any structure that emits heat in response to the control signal CTR. For example, the heater 230 may have various structures, as described below with reference to FIGS. 13A to 13C. For example, the calibrator 222 may turn on the heater 230 through the control signal CTR to cause the gas sensing device 210 to reach a calibration temperature $T_{CAL}$ when entering the calibration mode, and may turn off the heater 230 through the control signal CTR to cause the gas sensing device 210 to reach an ambient temperature when exiting the calibration mode.

The temperature sensing device 240 may sense the temperature of the gas sensing device 210, and may output a temperature signal (or temperature information) TEM corresponding to the sensed temperature. The temperature sensing device 240 may have any structure that senses the temperature of the gas sensing device 210. In some example embodiments, the temperature sensing device 240 may include a resonator of the same type as that included in the gas sensing device 210, the resonator having a resonant frequency that varies with temperature. The calibrator 222 may recognize the temperature of the gas sensing device 210 based on the temperature signal TEM. For example, the calibrator 222 may determine whether the gas sensing device 210 has reached the calibration temperature $T_{CAL}$ based on the temperature signal TEM, and may use the temperature signal TEM to obtain a plurality of resonant frequencies corresponding to a plurality of temperatures as in operation S34 of FIG. 11. For example, the controller 220 may adjust the resonant frequency of the gas sensing device 210 based on the temperature signal TEM from the temperature sensing device 240, in the sensing mode.

Figure 13A:
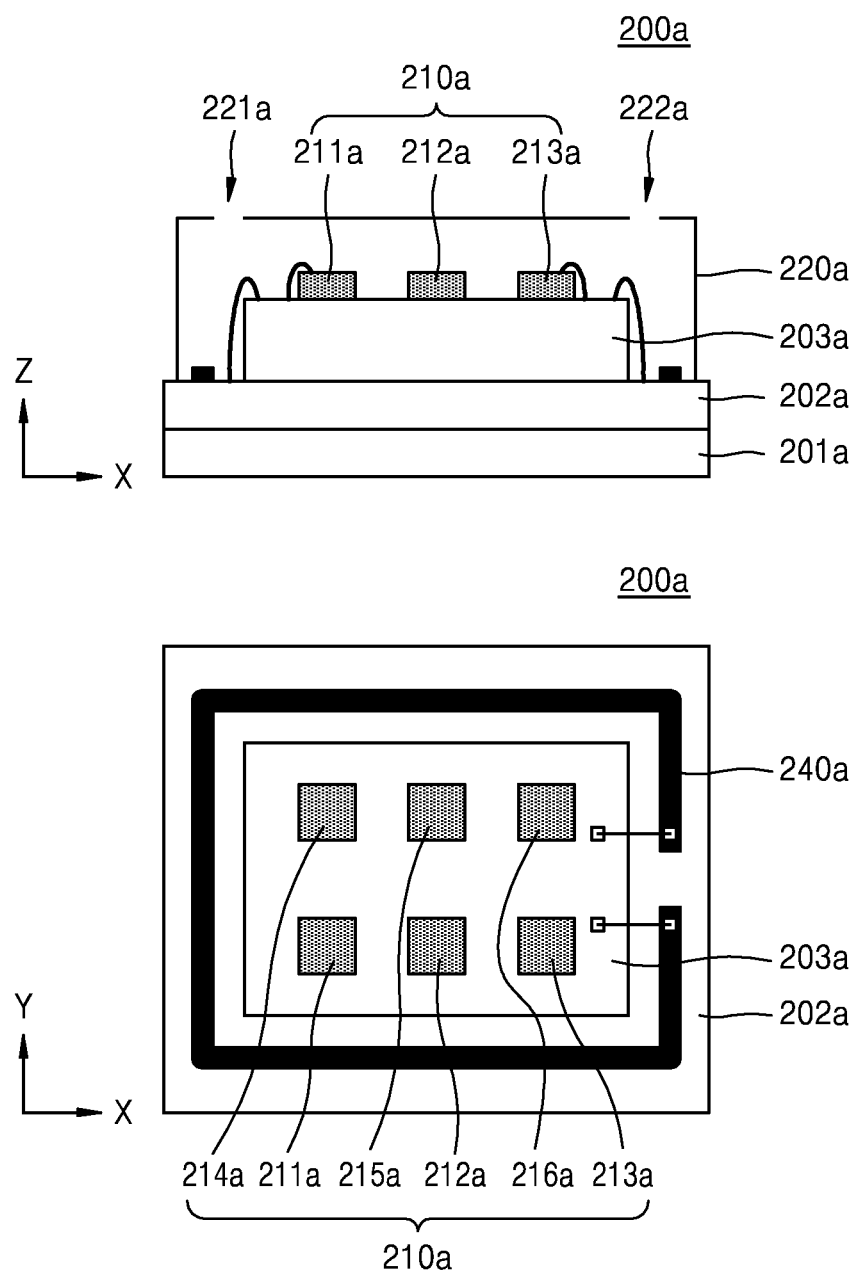
FIGS. 13A to 13C are views illustrating gas sensors according to some example embodiments.
Figure 13B:
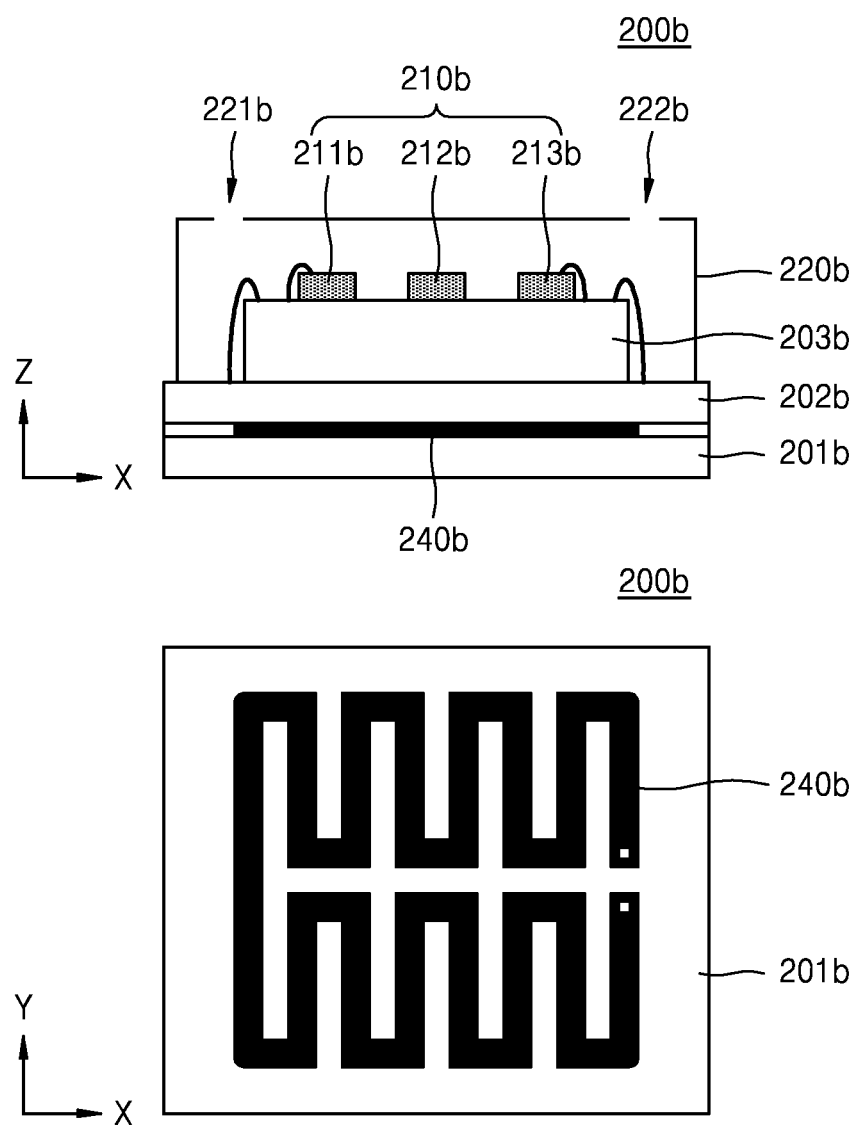
Figure 13C:
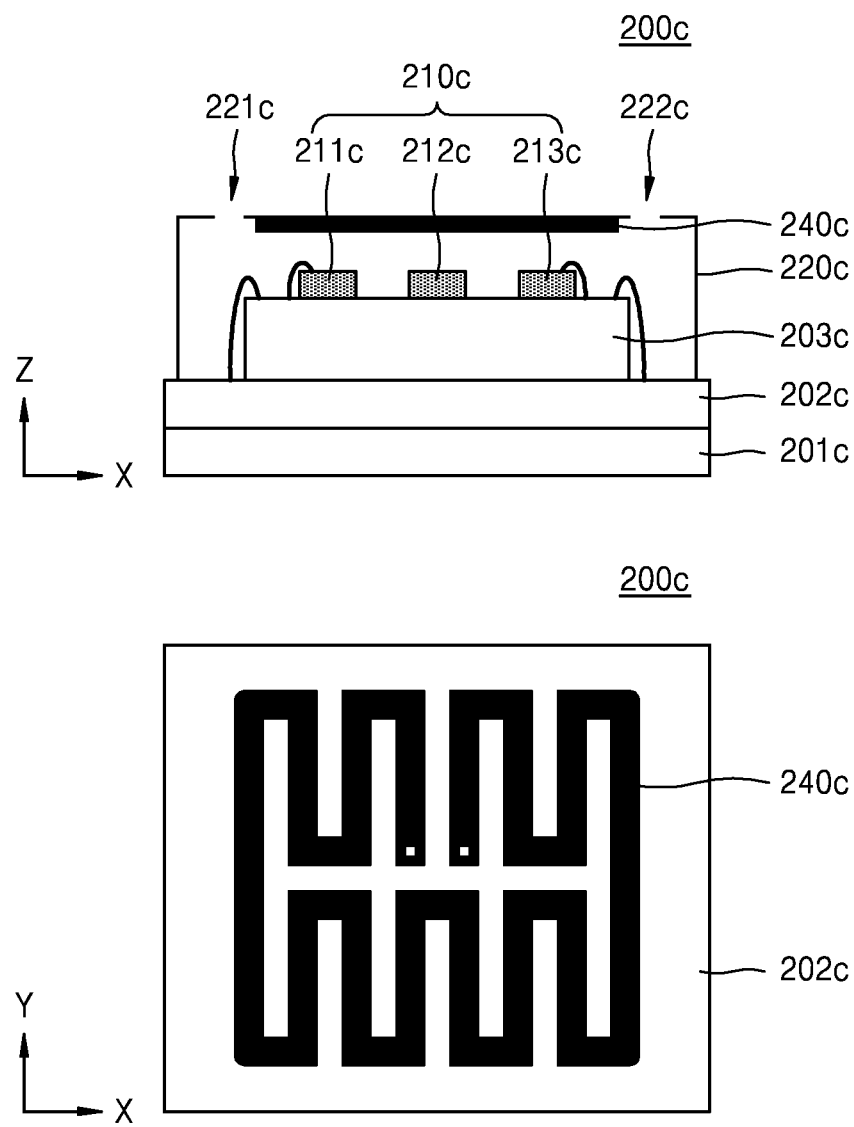

FIGS. 13A to 13C are views illustrating gas sensors 200a, 200b, and 200c according to some example embodiments. For example, drawings shown in the upper parts of FIGS. 13A to 13C illustrate cross-sectional views of the gas sensors 200a, 200b, and 200c, and drawings shown in the lower parts of FIGS. 13A to 13C illustrate heaters 240a, 240b, and 240c in top views of the gas sensors 200a, 200b, and 200c. In FIGS. 13A to 13C, an X-Y plane may be referred to as a horizontal plane and the Z-axis direction may be referred to as a vertical direction. A component arranged in +Z direction relative to another component may be referred to as being on the other component, and a component arranged in −Z direction relative to another component may be referred to as being under the other component. Illustration of some structures may be omitted in FIGS. 13A to 13C for convenience of illustration, and redundant descriptions among descriptions of FIGS. 13A to 13C are omitted.

Referring to FIG. 13A, the gas sensor 200a may include a solder pattern 201a, a bonding substrate 202a, a die 203a, and a resonator array 210a, which are sequentially arranged. The solder pattern 201a may include a solder pattern for solder connecting the gas sensor 200a to an external circuit, for example, a printed circuit board (PCB). The die 203a may be mounted on the upper surface of the bonding substrate 202a, and the bonding substrate 202a and the die 203a may be electrically connected to each other through a wire or the like. The die 203a may include a plurality of elements such as transistors formed through a semiconductor process. Although not specifically illustrated in FIG. 13A, the die 203a may include the controller 120 of FIG. 1.

The resonator array 210a may include a plurality of resonators 211a to 216a. For example, the gas sensing device 110 of FIG. 1 may include the resonator array 210a including the plurality of resonators 211a to 216a. In some example embodiments, each of the plurality of resonators 211a to 216a may include an FBAR. At least two of the plurality of resonators 211a to 216a may include different sensing materials, respectively, to sense different chemicals. Although FIG. 13A illustrates a resonator array 210a including six resonators, the resonator array 210a may include any number of resonators. A cover 220a may cover the resonator array 210a and the die 203a, and may include openings 221a and 222a through which gas passes.

The heater 240a for heating the resonator array 210a may be located on the upper surface of the bonding substrate 202a, as shown in the upper part of FIG. 13A. The heater 240a may surround the die 203a on the bonding substrate 202a, as shown in the lower part of FIG. 13A, and may be controlled by a controller (e.g., the controller 220 in FIG. 12) included in the die 203a. The shape of the heater 240a shown in FIG. 13A is merely an example, and in some example embodiments, the heater 240a may have any shape for heating the resonator array 210a on the bonding substrate 202a.

Referring to FIG. 13B, the gas sensor 200b may include a solder pattern 201b, a bonding substrate 202b, a die 203b, and a resonator array 210b, which are sequentially arranged. The resonator array 210b may include a plurality of resonators 211b, 212b, and 213b. A cover 220b may cover the resonator array 210b and the die 203b, and may include openings 221b and 222b through which gas passes.

The heater 240b for heating the resonator array 210b may be located between the upper surface of the solder pattern 201b and the lower surface of the bonding substrate 202b, as shown in the upper part of FIG. 13B. The heater 240b may also be located below the die 203b, as shown in the lower part of FIG. 13B, and may be controlled by a controller (e.g., the controller 220 in FIG. 12) included in the die 203b. The shape of the heater 240b shown in FIG. 13B is merely an example, and in some example embodiments, the heater 240b may have any shape between the upper surface of the solder pattern 201b and the lower surface of the bonding substrate 202b.

Referring to FIG. 13C, the gas sensor 200c may include a solder pattern 201c, a bonding substrate 202c, a die 203c, and a resonator array 210c, which are sequentially arranged, and the resonator array 210c may include a plurality of resonators 211c, 212c, and 213c. A cover 220c may cover the resonator array 210c and the die 203c, and may include openings 221c and 222c through which gas passes.

The heater 240c for heating the resonator array 210c may be located on the inner surface of the cover 220c, as shown in the upper part of FIG. 13C. The heater 240c may also be located over the resonator array 210c, as shown in the lower part of FIG. 13C, and may be controlled by a controller (e.g., the controller 220 in FIG. 12) included in the die 203c. The shape of the heater 240c shown in FIG. 13C is merely an example, and in some example embodiments, the heater 240c may have any shape on the inner surface of the cover 220c.

Figure 14:
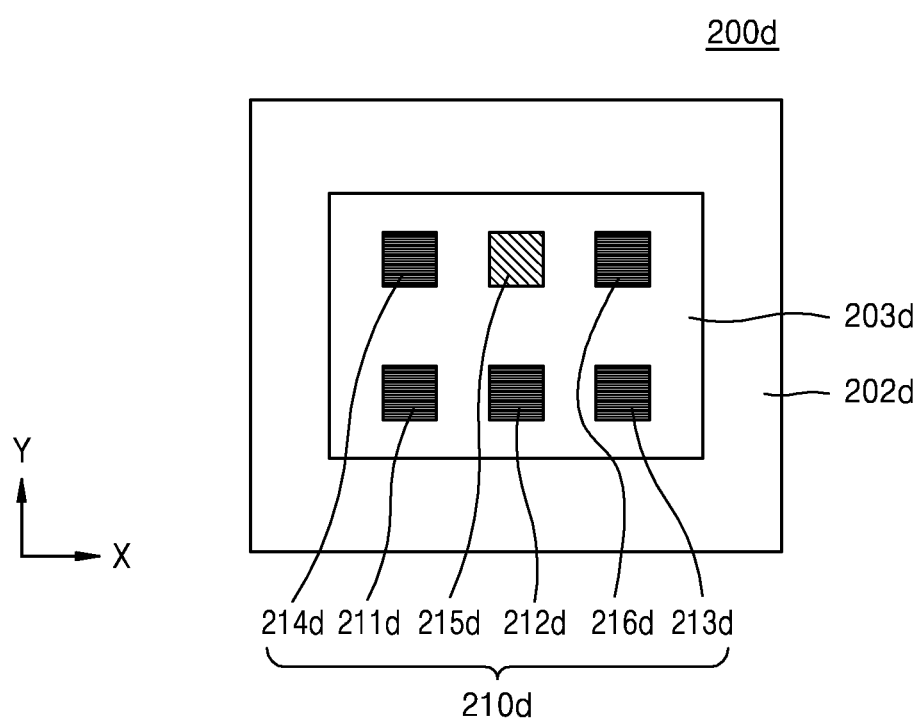
FIG. 14 is a view illustrating a gas sensor according to an example embodiment.

FIG. 14 is a view illustrating a gas sensor 200d according to an example embodiment. For example, FIG. 14 is a top view of the gas sensor 200d. Similar to the case described above with reference to FIG. 13A, the gas sensor 200d illustrated in FIG. 14 may include a bonding substrate 202d, a die 203d, and a resonator array 210d, and the resonator array 210d may include a plurality of resonators 211d to 216d. Hereinafter, the features or elements of FIG. 14, which are the same as those of FIGS. 13A to 13C, are omitted.

Referring to FIG. 14, the resonator array 210d may include the resonator 215d for temperature sensing. As described above with reference to FIG. 4 and the like, the resonant frequency of the resonator 215d may vary depending on the temperature, and a temperature sensing device (e.g., the temperature sensing device 240 in FIG. 12) for sensing the temperature of the resonator array 210d may include at least one of the plurality of resonators 211d to 216d of resonator array 210d. Accordingly, at least one of (e.g., 215d) the plurality of resonators 211d to 216d of the resonator array 210d may be a second resonator (e.g., the temperature sensing device 240 in FIG. 12), and the others (e.g., 211d, 212d, 213d, 214d, and 216d) of the plurality of resonators 211d to 216d may be a plurality of first resonators (e.g., the gas sensing device 210 in FIG. 12). In some example embodiments, the resonator 215d for temperature sensing may be capped with any material, for example, a shielding material (or a chemical-blocking material), unlike the resonators 211d, 212d, 213d, 214d, and 216d for gas sensing, in order to be blocked from gas and prevent resonant frequency variations due to gas.

Figure 15:
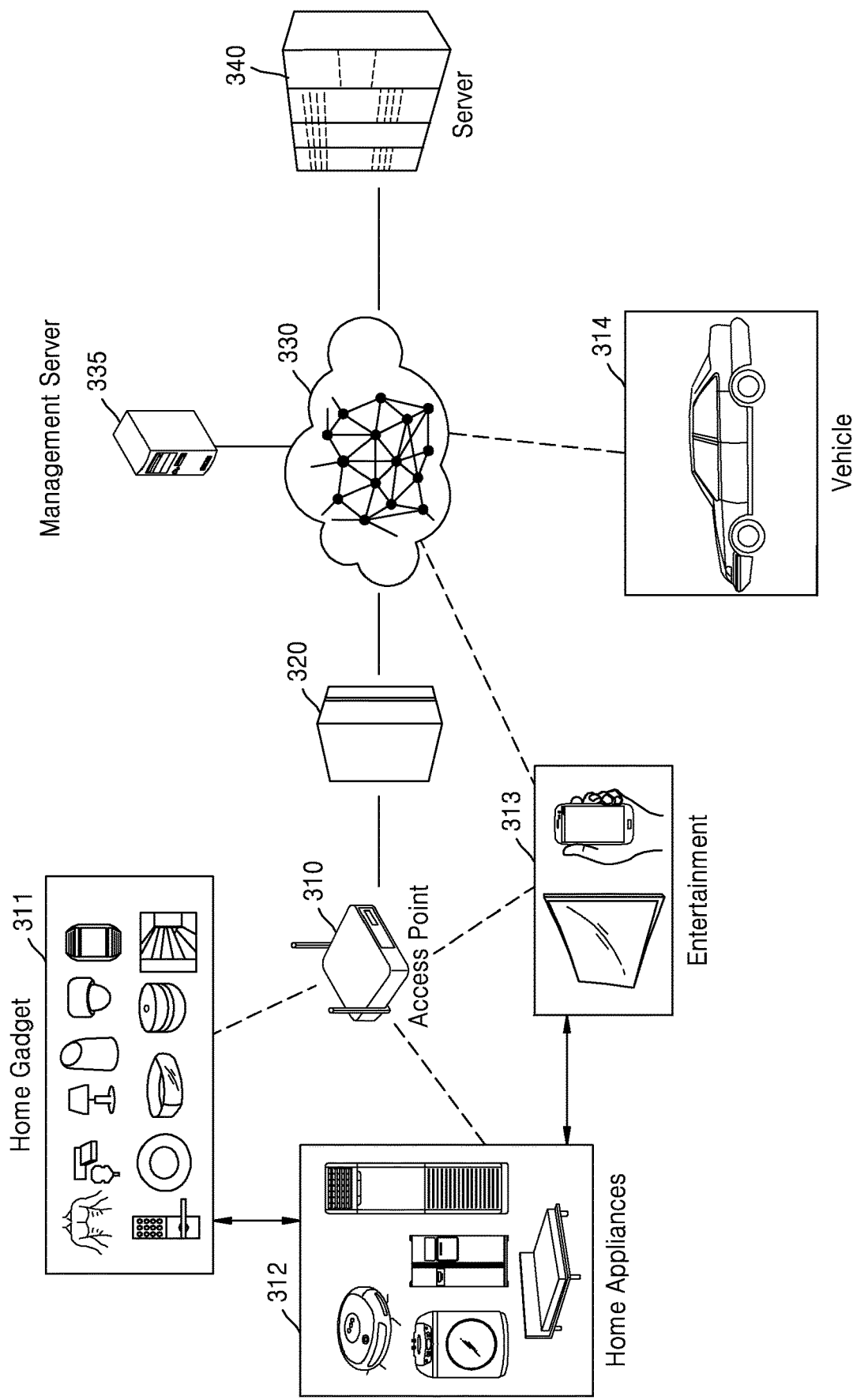
FIG. 15 is a view illustrating an Internet of Things (IoT) network system according to an example embodiment.

FIG. 15 is a view illustrating an Internet of Things (IoT) network system 300 according to an example embodiment. The IoT network system 300 of FIG. 15 may include entities including the gas sensor described above with reference to the drawings. As shown in FIG. 15, the IoT network system 300 may include a plurality of IoT devices 311, 312, 313, and 314.

Internet of things (IoT) may denote a network of objects using wired and/or wireless communication, and may be referred to as an IoT network system, a ubiquitous sensor network (USN) communication system, a machine type communication (MTC) system, a machine oriented communication (MOC) system, a machine to machine (M2M) communication system, a device to device (D2D) communication system, or the like. For example, the IoT network system 300 may include an IoT device, an access point, a gateway, a communication network, a server, and the like. Further, the IoT network system 300 may use a transmission protocol, such as user datagram protocol (UDP) and transmission control protocol (TCP), and an application protocol, such as IPv6 low-power wireless personal area networks (6LoWPAN) protocol, IPv6 internet routing protocol, constrained application protocol (CoAP), hypertext transfer protocol (HTTP), message queue telemetry transport (MQTT), and MQTT for sensors networks (MQTT-S), to exchange information between two or more components in the IoT network system.

In a wireless sensor network (WSN), each of the plurality of IoT devices 311, 312, 313, and 314 may be used as a sink node or a sensor node. The sink node may be referred to as a base station. The sink node may serve as a gateway for connecting the WSN to an external network (e.g., the Internet) and may assign a task to each sensor node and collect events detected by each sensor node. The sensor node may be a node in the WSN that may perform processing and gathering of sensory information, and may perform communication between nodes connected to each other in the WSN. In some example embodiments, the gas sensor described above with reference to the drawings may be included in the sensor node.

The plurality of IoT devices 311, 312, 313, and 314 may include an active IoT device that operates using its own power, and a passive IoT device that operates by power externally applied wirelessly. The active IoT device may include, but is not limited to, a refrigerator, an air-conditioner, a telephone, an automobile, and the like, and the passive IoT device may include, but is not limited to, a radio frequency identification (RFID) tag or an NFC tag. In some example embodiments, the IoT devices 311, 312, 313, and 314 may include passive communication interfaces such as a QR code, an RFID tag, and an NFC tag, or may include active communication interfaces such as a modem and a transceiver. Each of the plurality of IoT devices 311, 312, 313, and 314 may collect data by using a sensor such as the gas sensor described above with reference to the drawings, or transmit the collected data, for example, status information, to the outside via a wired and/or wireless communication interface and may transmit and/or receive control information and/or data via a wired and/or wireless communication interface.

In some example embodiments, each of the IoT devices 311, 312, 313, and 314 may form a group according to the characteristics of each IoT device. For example, the IoT devices 311, 312, 313, and 314 may be grouped into a home gadget group, a home appliance/furniture group, an entertainment group, or a vehicle group, and each of the IoT devices 311, 312, 313, and 314 may be included in a plurality of groups in common. For example, the home gadget group (e.g., the IoT device 311) may include a heart rate sensor patch, a blood glucose measuring device, a lighting device, a hygrometer, a surveillance camera, a smart watch, a security keypad, a temperature controller, a directional device, a window blind, and the like. The home appliance/furniture group (e.g., the IoT device 312) may include home appliances such as a robot cleaner, a washing machine, a refrigerator, an air conditioner, an air purifier, and a television and furniture such as a bed including a sensor. The entertainment group (e.g., the IoT device 313) may include a multimedia imaging device such as a television and a smart phone, and a communication device.

The IoT network system 300 may further include an access point 310. The plurality of IoT devices 311, 312, and 313 may be connected to a communication network through the access point 310 or may be connected to other IoT devices through the access point 310. In some example embodiments, the access point 310 may be embedded in one IoT device. For example, the access point 310 may be embedded in a television and a user may monitor or control at least one IoT device, connected to the access point 310, via a display of the television. Also, the access point 310 may be included in a mobile phone, and the mobile phone may function as an IoT device and as the access point 310 connected to other IoT devices and may be connected to a communication network through a mobile communication network or a local area wireless network.

The IoT network system 300 may further include a gateway 320. The gateway 320 may change a protocol to connect the access point 310 to an external communication network (e.g., the Internet network or a public communication network). The IoT devices 311, 312, and 313 may be connected to an external communication network through the gateway 320. In some example embodiments, the gateway 320 may be integrated into the access point 310. In other cases, the access point 310 may function as a first gateway and the gateway 320 may function as a second gateway. In some example embodiments, the gateway 320 may be included in one of the IoT devices 311, 312, and 313 and a mobile phone may function as an IoT device and as the gateway 320 connected to other IoT devices.

The IoT network system 300 may further include at least one communication network 330. For example, the communication network 330 may include the Internet and/or a public communication network, and the public communication network may include a mobile cellular network. The communication network 330 may provide a channel through which information collected by the IoT devices 311, 312, 313, and 314 is transmitted.

The IoT network system 300 may further include a server 340 and a management server 335 connected to the communication network 330. The communication network 330 may transmit data sensed by the IoT devices 311, 312, 313, and 314 to the server 340. The server 340 may store or analyze the data received through the communication network 330 and may transmit analyzed results through the communication network 330. The server 340 may store information associated with at least one of the IoT devices 311, 312, 313, and 314 and may analyze data, transmitted from a related IoT device, based on the stored information.

While the inventive concepts have been particularly shown and described with reference to some example embodiments thereof, it will be understood that various changes in form and details may be made therein without departing from the spirit and scope of the following claims.

What is claimed is:

1. A gas sensor comprising: a gas sensing device having a resonant frequency that varies with adsorbed chemicals; and processing circuitry configured to, detect the resonant frequency of the gas sensing device, generate current calibration data based on the resonant frequency of the gas sensing device which has been heated to a calibration temperature in a current calibration mode, the calibration temperature being a temperature at which the gas sensing device has the resonant frequency independent of concentrations of target gas chemicals, and adjust an output value thereof based on the current calibration data in a sensing mode.

2. The gas sensor of claim 1, wherein the processing circuitry is configured to
generate the current calibration data based on a first resonant frequency of the gas sensing device in a past calibration mode and a second resonant frequency of the gas sensing device in the current calibration mode.

3. The gas sensor of claim 2, wherein
the processing circuitry is further configured to calculate a frequency offset based on the first resonant frequency and the second resonant frequency, in the current calibration mode, and
the processing circuitry is further configured to add the frequency offset to the output value of the processing circuitry in the sensing mode.

4. The gas sensor of claim 2, wherein the processing circuitry is further configured to determine whether to generate the current calibration data based on the first resonant frequency and the second resonant frequency, in the current calibration mode.

5. The gas sensor of claim 4, wherein the processing circuitry is configured to generate the current calibration data when a ratio of the second resonant frequency to the first resonant frequency exceeds a reference value.

6. The gas sensor of claim 1, further comprising:
a data storage configured to store initial calibration data generated at a time of manufacturing the gas sensor, and the current calibration data,
wherein the processing circuitry is configured to adjust the output value thereof based on the current calibration data and the initial calibration data.

7. The gas sensor of claim 1, further comprising:
a heater configured to heat the gas sensing device,
wherein the processing circuitry is configured to control the heater to heat the gas sensing device in the current calibration mode.

8. The gas sensor of claim 7, wherein the processing circuitry is further configured to collect a plurality of resonant frequencies at a plurality of temperatures of the gas sensing device and set the calibration temperature based on the collected plurality of resonant frequencies, in the current calibration mode.

9. The gas sensor of claim 7, further comprising:
a temperature sensing device configured to sense a temperature of the gas sensing device and output a temperature signal,
wherein the processing circuitry is configured to control the heater such that the gas sensing device reaches the calibration temperature based on the temperature signal from the temperature sensing device, in the current calibration mode.

10. The gas sensor of claim 9, wherein
the temperature sensing device has a resonant frequency that varies with temperature,
the gas sensor includes a resonator array, which includes a plurality of first resonators of a plurality of gas sensing devices including the gas sensing device and at least one second resonator of the temperature sensing device.

11. The gas sensor of claim 10, wherein the second resonator of the temperature sensing device is capped with a chemical-blocking material.

12. The gas sensor of claim 9, wherein the processing circuitry is further configured to adjust the resonant frequency of the gas sensing device based on the temperature signal from the temperature sensing device, in the sensing mode.

13. The gas sensor of claim 1, comprising:
a substrate;
a die having an upper surface on which the gas sensing device is located, the die on an upper surface of the substrate and including the processing circuitry; and
a cover covering the die and the gas sensing device, the cover including at least one opening.

14. The gas sensor of claim 13, further comprising:
a heater configured to heat the gas sensing device,
wherein the heater is on at least one of the upper surface of the substrate, a lower surface of the substrate, or an inner surface of the cover.

15. The gas sensor of claim 1, wherein the gas sensing device comprises a film bulk acoustic resonator (FBAR) including an exposed sensing material.

16. The gas sensor of claim 1, wherein the processing circuitry is further configured to enter the current calibration mode periodically.

17. A gas sensor comprising: a gas sensing device having a resonant frequency that varies with adsorbed chemicals; a heater configured to heat the gas sensing device; and a controller configured to, control the heater such that the gas sensing device reaches a calibration temperature, the calibration temperature being a temperature at which the gas sensing device has the resonant frequency independent of concentrations of target gas chemicals, generate calibration data based on the resonant frequency in a calibration mode, and detect gas based on the calibration data and the resonant frequency in a sensing mode.

18. A method of sensing gas, the method comprising: heating a gas sensing device, which is configured to have a resonant frequency that varies with adsorbed chemicals, to a calibration temperature in a current calibration mode, the calibration temperature being a temperature at which the gas sensing device has the resonant frequency independent of concentrations of target gas chemicals; generating current calibration data based on the resonant frequency of the heated gas sensing device in the current calibration mode; and detecting gas based on the current calibration data and the resonant frequency of the gas sensing device as to which the heating has been stopped, in a sensing mode.

19. The method of claim 18, wherein the generating comprises generating the current calibration data based on a first resonant frequency of the gas sensing device detected in a past calibration mode and a second resonant frequency of the gas sensing device detected in the current calibration mode.

* * * * *